United States Patent [19]
Parker et al.

[11] Patent Number: 4,955,391
[45] Date of Patent: Sep. 11, 1990

[54] FLUID MONITORING APPARATUS

[75] Inventors: Robert L. Parker; Charles G. Reed, both of Oklahoma City, Okla.

[73] Assignee: Invenomed, Inc., Oklahoma City, Okla.

[21] Appl. No.: 333,468

[22] Filed: Apr. 5, 1989

Related U.S. Application Data

[63] Continuation-in-part of Ser. No. 78,792, Jul. 27, 1987, abandoned.

[51] Int. Cl.$^5$ .............................................. A61B 5/00
[52] U.S. Cl. ..................................... 128/771; 604/319
[58] Field of Search ............................... 128/760, 771; 604/319–321, 53

[56] References Cited

U.S. PATENT DOCUMENTS

| 3,648,698 | 3/1972 | Doherty | 604/319 |
| 3,680,560 | 8/1972 | Pannier et al. | 604/320 |
| 3,727,603 | 4/1973 | Holbrook | 128/771 |
| 3,871,231 | 3/1975 | Ciarico | 128/771 |
| 3,998,227 | 12/1976 | Holbrook et al. | 604/319 |
| 4,417,585 | 11/1983 | Frank | 128/771 |
| 4,487,606 | 12/1984 | Leviton et al. | 604/319 |
| 4,608,996 | 9/1986 | Brown | 128/760 |
| 4,723,946 | 2/1988 | Kay | 604/53 |
| 4,813,931 | 3/1989 | Hauze | 128/760 |

Primary Examiner—Max Hindenburg
Attorney, Agent, or Firm—Glen M. Burdick

[57] ABSTRACT

A fluid monitoring apparatus has a canister into which fluid is introduced via an entry port at the top of the canister, a conventional volume measuring assembly within the canister and a flow control assembly that receives the fluid from the entry port and discharges the fluid at a controlled rate into the volume measuring assembly. The canister has a tubular body portion made of transparent plastic on which volume indicia are inscribed and is closed at its ends by a cover plate in which the entry port is formed and a floor plate in which a discharge port is formed. A pump connected to the discharge port is operable for removing fluid from the canister and is flushed with antiseptic solution via a second pump. The flow control assembly has a partition that extends across the interior of the canister and has an upwardly extending flange to form a fluid catchment and an integral funnel that discharges into the volume measuring assembly. A filter is provided across the canister or funnel. A suction port is formed in the cover plate and separated from the entry port by a partition that extends across a perforated cup that is secured to the cover plate about both ports and encircled by a tubular splash shield. Probes, including a pH probe in the cover plate, extend into the canister and an injection port is formed in lower portions of the canister.

10 Claims, 3 Drawing Sheets

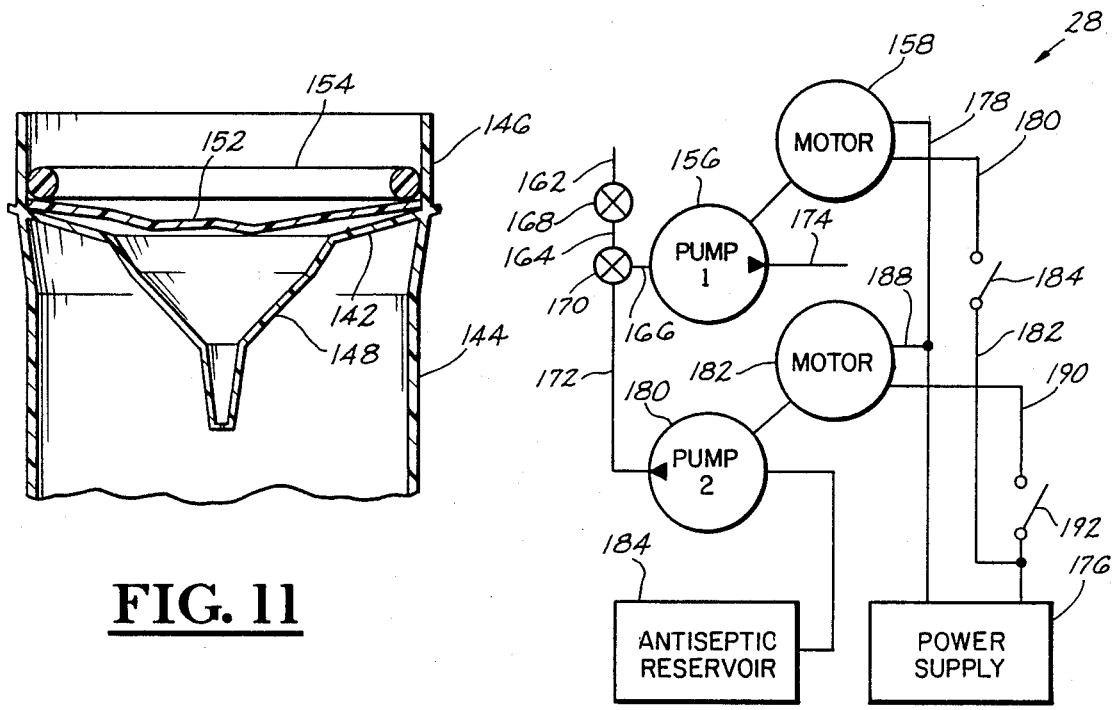
FIG. 11
FIG. 13
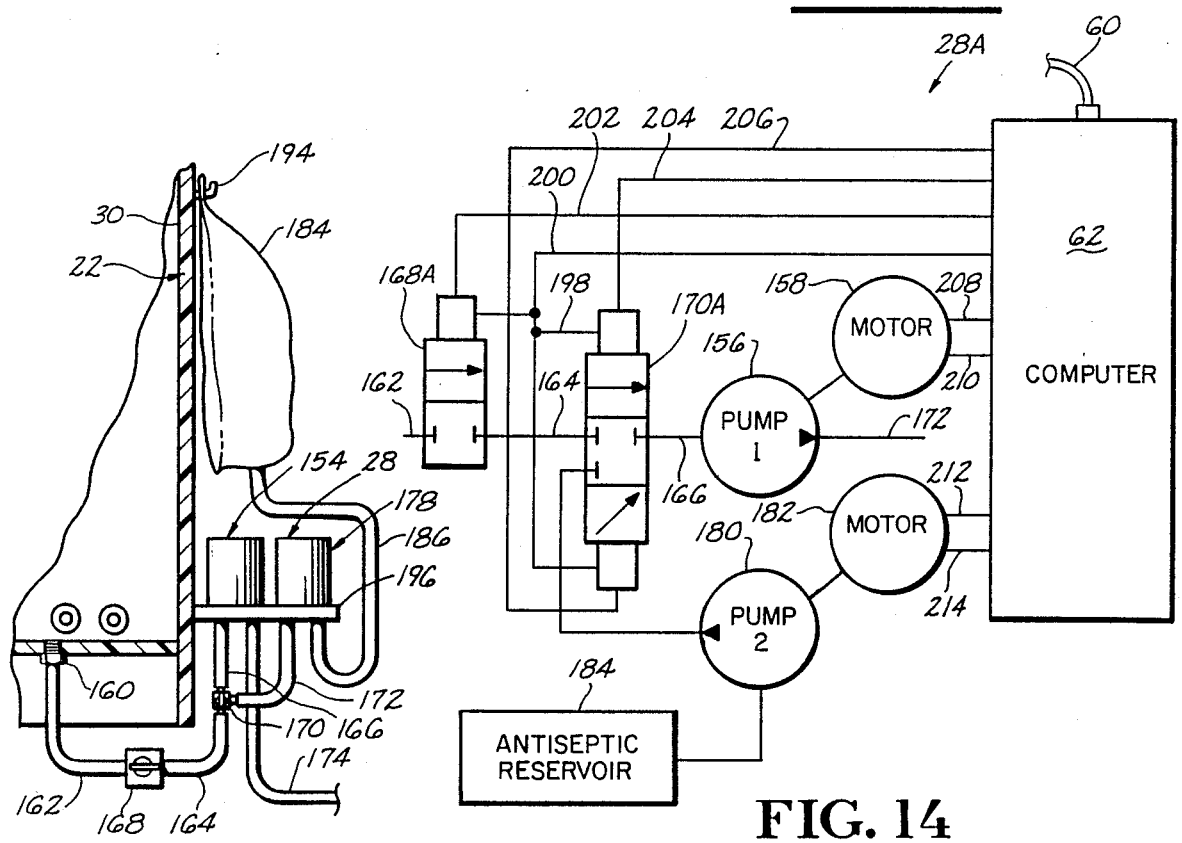
FIG. 12
FIG. 14

FLUID MONITORING APPARATUS

CROSS REFERENCE TO RELATED APPLICATIONS

The present U.S. Pat. No. is a continuation-in-part of the U.S. Pat. No. entitled Computerized Electronic Monitoring Urometer, Serial No. 07/078,792, filed July 27, 1987, now abandoned, by Robert L. Parker and Charles G. Reed.

BACKGROUND OF THE INVENTION

1. Field of the Invention

The present invention relates qenerally to improvements in fluid monitoring apparatus, and, more particularly, but not by way of limitation, to apparatus for monitoring the volume of fluid received from the body of a human patient.

2. Brief Description of the Prior Art

In the treatment of patients for various illnesses, it is often important that the physician know the rate at which urine is secreted by the patient's kidneys. For example, monitoring urine output provides the physician not only with information relating to renal functioning but, in addition, provides him with information relating to the functioning of other organs, the effects of drugs and the effectiveness of the course of treatment the patient is under going. In general, then, urine monitoring is a valuable tool for both the diagnosis and treatment of disease.

Because of the value of urine monitoring to the physician, a variety of urine monitoring devices have been developed and these devices have, in general, served the physician well, especially since the advent of the use of computers in medical treatment. With the coupling of flow measuring devices to computers, the physician has been given a tool that enables him to keep a constant, easily retrievable record of the condition and progress of his patient.

However, urine monitoring apparatus has, in one respect, lagged behind the capabilities that are provided by the use of computers in medicine. While the devices currently available serve the purpose of monitoring urine flow very well, they are special purpose devices that cannot be adapted to other purposes for which an accurate record of fluid flow would be of value to the physician. For example, during surgery, a physician will often measure the loss of blood by the patient by withdrawing fluid, including saline solution, from the open wound so that the blood loss can be determined from the difference in the quantities of fluid withdrawn and the quantity of saline solution introduced. At present, no suitable apparatus capable of making measurements with the accuracy and speed comparable to that of a uroflowmeter exists for making such a measurement. A uroflowmeter which might otherwise be used this purpose to provide the desired accuracy and speed is incapable of handling the rate of flow that occurs when fluid is actively drawn from a wound. Similarly, because of the special purpose for which uroflowmeters have been designed, they are generally incapable of being adapted to provide information concerning other fluid parameters in which the physician might, at various times be interested.

SUMMARY OF THE INVENTION

The present invention provides a general purpose fluid monitoring apparatus that can be used in substantially any set of circumstances in which a computer can be used to directly provide information concerning a fluid derived from a patient. For example, the apparatus of the present invention is capable of enabling the measurement of fluid volumes received from a patient at both the low flow rate associated with urine discharge and, without loss of accuracy or speed of measurement, equally capable of enabling measurement of fluid volume when suction is applied to a wound to withdraw a mixture of saline solution that has been introduced into the wound and blood that has seeped into the wound. Moreover, the apparatus is readily adapted to the measurement of other fluid parameters; for example pH of the fluid, and to the sampling of the fluid as well as to the adjustment of characteristics of the fluid within the apparatus. Thus, in general, the present invention provides an inexpensive fluid monitoring apparatus that has a wide variety of applications and can be used with a computer to rapidly provide the physician with a broad range of diagnostic information about fluid derived from a patient.

To these and other ends, the apparatus of the present invention is comprised of a canister having an entry port formed in the upper end thereof so that fluid discharged by or withdrawn from a patient may be introduced into the upper end of the canister via the entry port. Below the entry port, the apparatus is provided with a flow limiter which, in one preferred embodiment, has the form of a partition that extends across the interior of the canister and is provided with a tubular flange to form a catchment for the fluid which is then released at a controlled rate by a funnel formed integrally in the partition. Underlyinq the funnel is an electronically sensible volume indicating assembly, preferably of the bistable, tilting bucket type, that can be connected to a computer to measure increments of fluid introduced into the volume indicating assembly. By internally limiting the flow rate of fluid to the volume indicating assembly, the apparatus can measure volumes of fluid introduced into the apparatus at a high flow rate, characteristic of removal of fluid from a wound during surgery, without loss of accuracy arising from limitations of the capacity of the volume indicating assembly and without loss of the capability of the volume indicating assembly to measure low flow rates characteristic of the discharge of urine from the kidneys. Thus, the volume indicating assembly can be selected on the basis of accuracy and cost while still providing the apparatus with the capability of handling the wide range of flow rates into the apparatus that will enable the apparatus to be used for a wide range of medical applications involving the computerized monitoring of fluid flow.

Additionally, the canister can be readily adapted to provide additional information to the physician. Thus, for example, an injection port formed in the canister permits ready withdrawal of samples of the fluid in the canister for laboratory tests without the danger of infection that occurs when a fluid collection apparatus attached to the human body is opened to the environment. Similarly, probe ports can be formed in the canister to enable the mounting of probes, connectable to a computer, for sensing various fluid parameters with a example being the pH of the fluid.

Moreover, the low cost aspect of the apparatus, achievable in part by the ease of construction of the canister to be described below and in part by the capability of the apparatus to use an inexpensive volume indicating assembly, provides the apparatus with a flexibility relating to the environment in which such an apparatus might be used. In environments in which the cost of providing extensive medical facilities might be high; for example, in a field hospital, the apparatus can be constructed using adhesives to provide necessary seals and structural integrity and packed in sterile containers for one time use after which it is discarded. Conversely, where sterilization equipment will be available, the apparatus can be constructed to enable disassembly, without loss of sealing during use, so that the apparatus can be easily sterilized after one use for subsequent use with another patient.

An object of the invention is thus to provide a fluid monitoring apparatus that can be used in a wide range of medical applications involving the measurement of a wide range of fluid flow rates.

Another object of the invention is to provide a fluid monitoring apparatus that can be economically adapted for use in a variety of environments having a range of levels of available facilities for patient care.

A further object of the invention is to provide a fluid monitoring apparatus which can be readily and economically adapted to the measurement of a number of fluid parameters.

Still another object of the invention is to provide a low cost fluid monitoring apparatus having a high degree of flexibility with respect to medical application, environment and parameters to be measured.

Other objects, features and advantages of the present invention will become apparent from the following detailed description when read in conjunction with the drawings and appended claims.

BRIEF DESCRIPTION OF THE DRAWINGS

FIG. 11 is a fragmentary cross section of a modified flow rate controller.

FIG. 12 is a fragmentary side elevational view illustrating a canister discharge assembly of the apparatus of FIG. 1.

FIG. 13 is one preferred form of the hydraulic and electrical circuit of the canister discharge assembly of FIG. 12.

FIG. 14 is an alternative hydraulic and electric circuit for the canister discharge assembly.

DESCRIPTION OF THE PREFERRED EMBODIMENT

Figure 1:
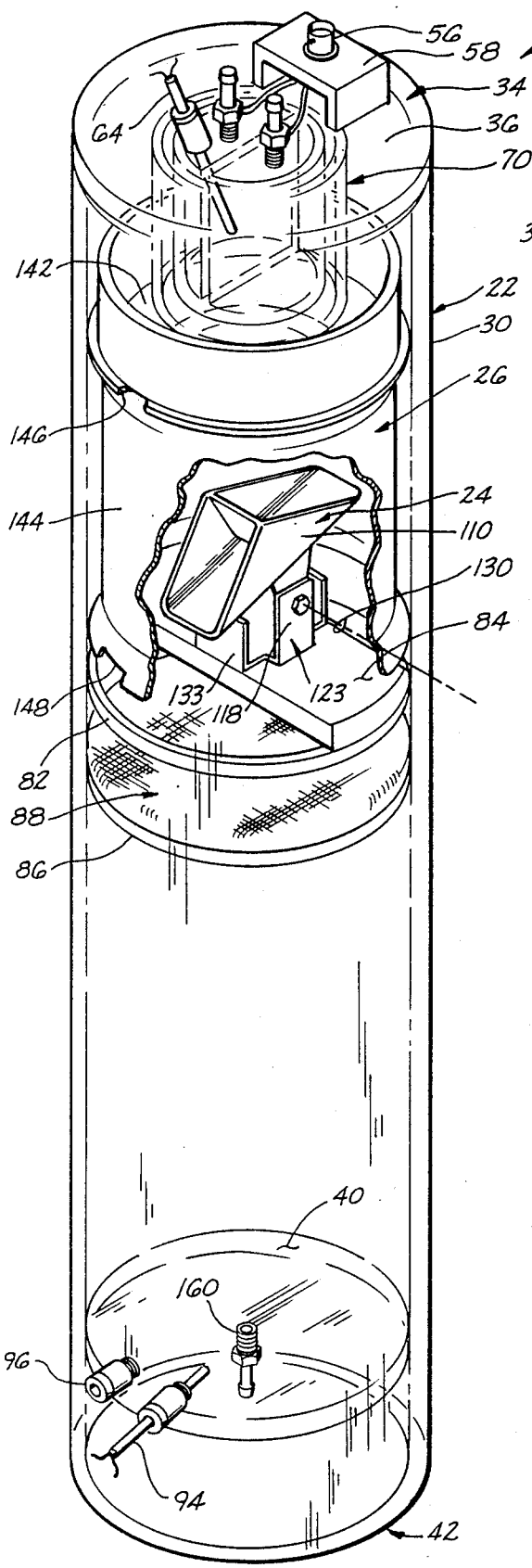
FIG. 1 is an isometric view of one preferred embodiment of a fluid monitoring apparatus constructed in accordance with the present invention.
Figure 2:
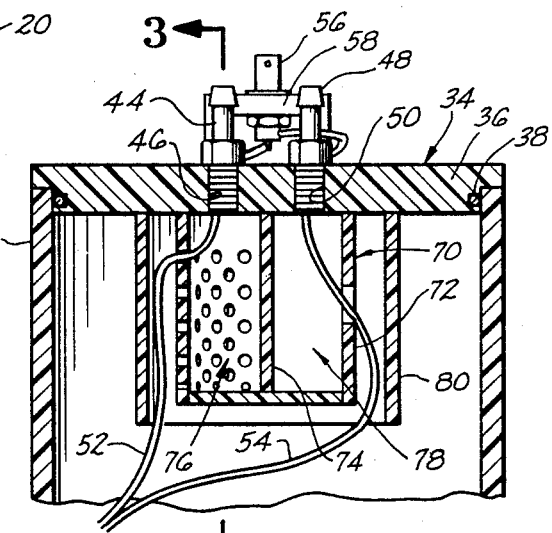
FIG. 2 is a fragmentary cross section in side elevation of upper portions of the apparatus of FIG. 1.

Referring now to the drawings in general and to FIG. 1 in particular, shown therein and designated by the general reference number 20 is a fluid monitoring apparatus constructed in accordance with the present invention. In general, the apparatus 20 is comprised of a canister 22 that is more particularly illustrated in FIGS. 2 through 6, a volume indicator assembly 24 that is more particularly shown in FIGS. 7 through 9, and flow rate controller 26 that is more particularly shown in FIGS. 10 and 11. In use, fluids received from a patient will be collected in the canister 20 and such fluids can be discharged from the canister 20 via a fluid discharge assembly that has been illustrated in two embodiments designated by the numerals 28 and 28A in FIGS. 12 through 14.

With continuing reference to FIG. 1, the canister 22 is comprised of a tubular body portion 30 that is preferably constructed of a clear plastic, such as a methacrylate resin, so that the level of fluid in the canister 22 can be easily observed at any time. Volume indicia 32 can be inscribed on the body portion 30 to permit a quick estimate of the quantity of fluid the canister contains. A more accurate measure of such quantity is provided in a manner to be described below.

The canister 22 has an upper end 34 which is closed by a cover plate 36 that can, like the body portion 30, be constructed of a suitable plastic. It is contemplated that the canister 22 will be sealed while it is being used to collect body fluids to prevent infectious organisms from entering the body via the apparatus 20. To this end, a portion of the cover plate 36 can be extended into the upper end of the body portion 36 and provided with a O-ring seal as indicated at 38 in FIGS. 2 and 3. When sealed in this manner, the cover plate 36 can be removed from the body portion 30 for cleaning and reuse of the apparatus 20. In circumstances in which the apparatus is packaged and shipped for one-time use, sealing of the cover plate 36 to the body portion 30 can be effected by cementing the cover plate 36 to the upper end of the body portion 30. The lower end of the canister 22 is closed and sealed by a plastic floor plate 40 that is cemented within the tubular body portion 30 so that the floor plate extends laterally across lower portions of the interior of the canister 22 near the lower end 42 thereof.

To provide for the introduction of fluid into the upper end 34 of the canister 22, an entry port is formed in the cover plate by a tubular, metal tubing connector 44 that is screwed into a threaded bore 46 formed through the cover plate 36. Similarly, a tubular, metal tubing connector 48 is screwed into a threaded bore 50 to provide a suction port by means of which the pressure in the canister 22 can be reduced. Thus, fluid can be actively drawn into the canister via the entry port by suction applied to the suction port or introduced passively by closing the suction port with, for example, a length of surgical tubing and a tubing clamp. Sealing of the connectors 44 and 48 to prevent an avenue of infection to a patient using the apparatus 20 can be effected by applying a sealing compound the to connectors 44 and 48 before screwing them into the bores 46 and 50.

Figure 7:
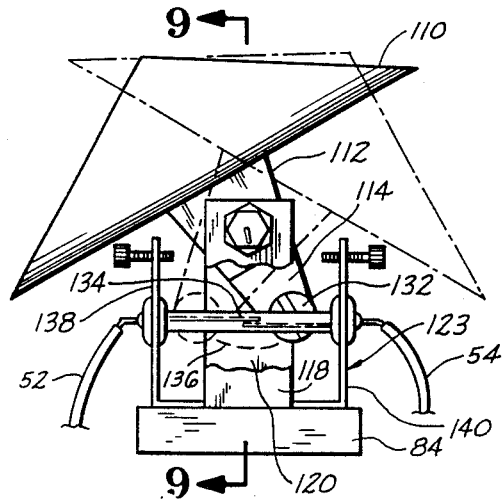
FIG. 7 is a side elevational view in partial cutaway of the volume indicating assembly of the apparatus of FIG. 1.

As will be discussed below, the volume indicator assembly 24 is constructed to provide electrically sensible indications of successive, equal volume increments of fluid introduced into the canister 22 and the construction of the tubing connectors 44 and 48 of metal facilitates the sensing of these increments. In particular, insulated wires 52 and 54 soldered to the connectors 44 and 48 within the canister 22 extend to the volume indicator assembly 24 as shown in FIG. 7 to provide conducting paths to the assembly 24. Exteriorly of the canister, the tubing connectors 44 and 48 are wired to an electrical connector 56 mounted on a plastic, inverted U-shaped support 58 cemented to the cover plate 36. In use, an electrical cable 60 (FIG. 14) having a connector that mates with the connector 56 can be utilized to provide the volume indications to a suitable counting device; in particular, to a computer 62 that is programmed to count and display the volume of fluid in the canister 22.

In the preferred embodiment of the apparatus 20, a pH probe 62 can be mounted on the canister to extend through the cover plate 36 and the sensing end of the probe 64 is positioned directly below the entry port to be continuously washed by fluid introduced into the canister 22. To this end, a tubular probe mount 66, into which the probe 64 can be screwed, is cemented to the cover plate 36 adjacent the connector 44 at an angled to provide the described positioning of the probe 64. A bore 68 is formed through the cover plate 36 to pass the probe 64 therethrough so that electrical connections can be made to the probe 64 exteriorly of the canister 22. As in the case of the volume indicator assemble 24, the probe 64 is preferably connected to the computer 62 so that a continuous display of the pH of the fluid can be provided to the user of the apparatus 20.

Figure 3:
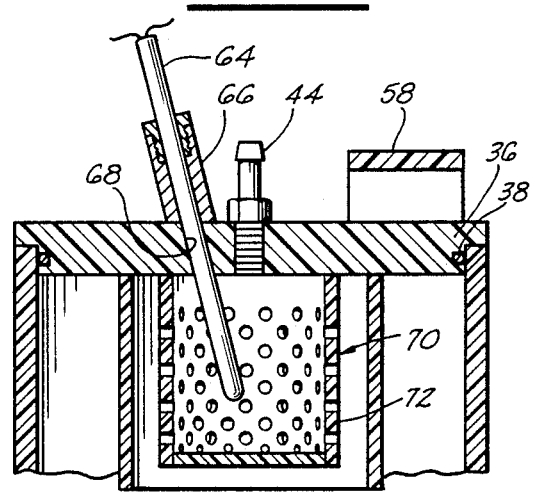
FIG. 3 is a fragmentary cross section taken along line 3—3 of FIG. 2.

Within the canister 22, the apparatus 20 is provided with a fluid separator 70 that prevents fluid drawn into the canister 22 under suction from being drawn from the suction port provided by the connector 48. To this end, the separator 70 is comprised of a perforated cup 72 that is cemented to the underside of the cover plate 36 to extend about the entry and suction ports as shown in FIG. 3 and a partition plate 74 that is cemented diametrically across the cup 72 to divide the interior of the cup into non-communicating entry and suction chambers 76 and 78. The perforations in the cup walls serve to fluidly communicate both of the chambers 76 and 78 to the interior of the canister 22 and further provide for passage of the wires 52 and 54 from the connectors 44, 48 to the volume indicator assembly 24. A tubular splash shield 80 is cemented to the cover plate 36 in a surrounding, concentric relation to the cup 72 to prevent fluid drawn into the canister 22 under suction from impinging on the inner wall of the tubular portion, 30 of the canister 22 and running down the wall to lower portions of the canister 22 without first passing through the volume indicator assembly 24. Thus, the splash shield insures that all fluid introduced into the canister 22 will be monitored.

Figure 4:
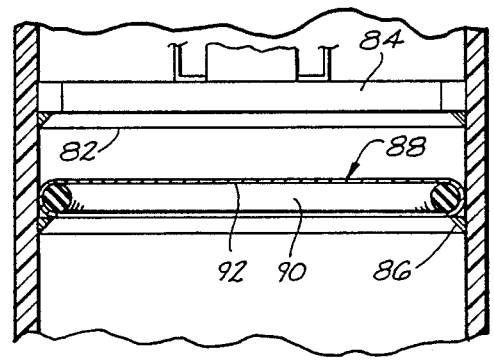
FIG. 4 is a fragmentary cross section in side elevation of central portions of the apparatus of FIG. 1.

In the version of the apparatus 20 that is constructed for re-use, a ledge is formed on the inner wall of central portions of the tubular portion 30 of the canister 22 by cementing a plastic ring 82 to such wall, as shown in FIGS. 1 and 4, to support the volume indicator assembly 24 within the canister 22. To this end, the volume indicator assembly includes a support member 84 that extends diametrically across the interior of the canister 22 and is, in turn, supported by the ring 82. Thus, the volume indicator assembly 24 can be easily removed from the canister 22 by removing the cover plate 36 and withdrawing the volume indicator assembly 24 through the upper end of the tubular portion 30. When the apparatus 20 is constructed for one-time use, the support member 84 can conveniently be cemented to the interior wall of the tubular portion 30.

An additional ledge, below the ring 82, can be provided by a ring 86 similarly cemented to the inner wall of the tubular portion 30. In many circumstances, it will be desired to filter the fluid introduced into the canister 22 and such filtering can be provided by a filter 88 that rests atop the ring 86. In many cases, a suitable form for the filter 88 is a plastic 0-ring 90 to which is cemented a porous membrane 92. More specifically, the membrane 92 can be made of finely woven silk cloth.

Figure 5:
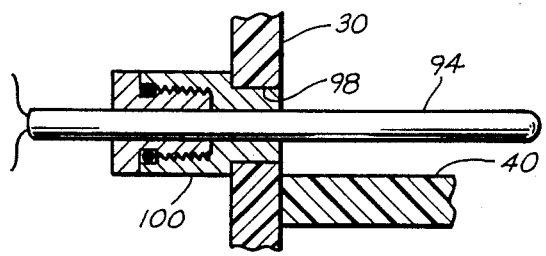
FIG. 5 is a cross section in side elevation of a sensor assembly mounted in the canister of the apparatus.
Figure 6:
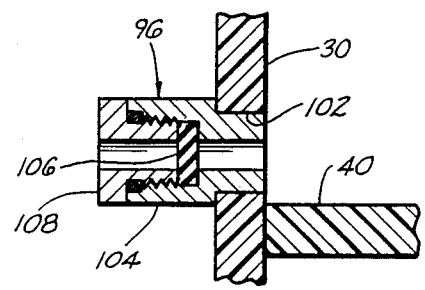
FIG. 6 is a cross section in side elevation of an injection port assembly mounted in the canister of the apparatus.

With continuing reference to FIG. 1 and with additional reference to FIGS. 5 and 6, the apparatus 20 can be further provided with an additional sensor probe 94 that can be utilized to measure any of a variety of parameters associated with the fluid introduced into the canister 22 and an injection port assembly 96 that permits sampling of such fluid or the introduction of materials into the fluid. Examples of additional parameters of the fluid that might be measured are specific gravity and the concentration of a selected ion. In general, the probe 94 can be any sensor that can measure any parameter that can be detected with an electrical probe connectable to the computer 62. An example of the use of the injection port assembly 96, in addition to withdrawal of fluid for chemical testing, is the introduction of an anticoagulant at times that the canister contains blood.

To mount the probe 94 on the canister 22, a sensor probe opening 98 is formed through the wall of the tubular body portion 30 adjacent the floor plate 40 to receive a tubular coupler 100 which is cemented into the opening 98. As shown in FIG. 5, the coupler 100 has a threaded bore into which the probe 94 can be conveniently screwed so that the fluid parameter sensing end of the probe is positioned within the canister 22 and electrical connections can be made to the probe exteriorly of the canister. In the preferred use of the apparatus 10, the probe 94 will be connected to the computer 62 so that the value of the measured parameter can be displayed at any time.

The injection port assembly 96 is similarly mounted in an injection opening 102 formed through the wall of the canister tubular portion 30 adjacent the floor plate 40 and is comprised of a tubular coupler 104 cemented into the opening 102 and having a bore in which an elastomeric disc 106 is secured to extend across the opening 102 by a tubular cap 108 that screws into the bore of the coupler 104.

Figure 8:
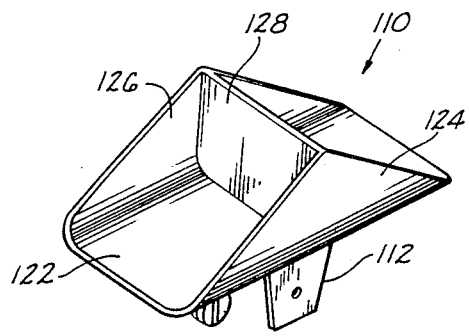
FIG. 8 is an isometric view of the fluid receiver of the volume indicating assembly.
Figure 9:
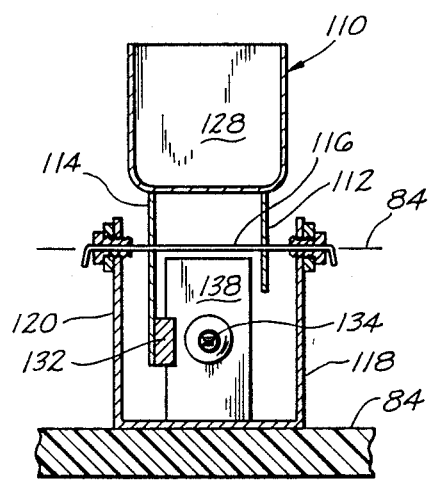
FIG. 9 is a cross section of the volume indicating assembly taken along line 9—9 of FIG. 7.

Coming now to the volume indicator assembly 24, such assembly is comprised of a fluid receiver 110 mounted on the support member 84 for pivotation between positions shown in solid and dashed lines in FIG. 7. To this end, the receiver 110 has depending, apertured legs 112, 114 that are mounted on a wire 116 that extends between upturned legs 118 and 120 of a generally cruciform receiver support 123. As shown in FIG. 8, the receiver 110 has a floor 122 and triangular sides 124, 126 and is divided into two bucket portions, by partition 128, that can alternatively collect fluid in the two positions shown in FIG. 7, such fluid being dumped in the other position of the receiver 110. The bucket portions are balanced so that the receiver is stable in either of the two positions shown in FIG. 7 and the pivotation axis 130 of the receiver is located so that the introduction of a selected increment of fluid into the bucket portion positioned to collect fluid will cause an imbalance sufficient to tip the receiver to the other position. Thus, a flow of fluid to the receiver will cause the bucket portions to alternatively collect the selected increment of fluid with the receiver pivoting between the two positions between collections of successive increments. A magnet 132 is mounted on the receiver leg 114 and a normally open, magnetically closable reed switch 134 is mounted adjacent the path 136 of travel of the magnet 132 via upstanding legs 138, 140 of the receiver support 123. The reed switch 134 is electrically connected to the wires 52 and 54 to thus provide an electrically sensible indication of each fluid increment to the computer 62.

An important aspect of the apparatus 20 is that accurate fluid measurements that can be effected by the volume indicator assembly 24 not be limited to circumstances in which low flow rates of fluid are introduced into the canister 22. Rather, it is contemplated that higher flow rates that might occur when fluid is drawn into the canister 22 by suction can also be measured with an accuracy stemming from the construction of the volume indicator assembly 24. The flow rate controller serves to enable use of the apparatus 20 during high flow rate conditions without loss of accuracy of measurement of the volume of fluid introduced into the canister 22.

Figure 10:
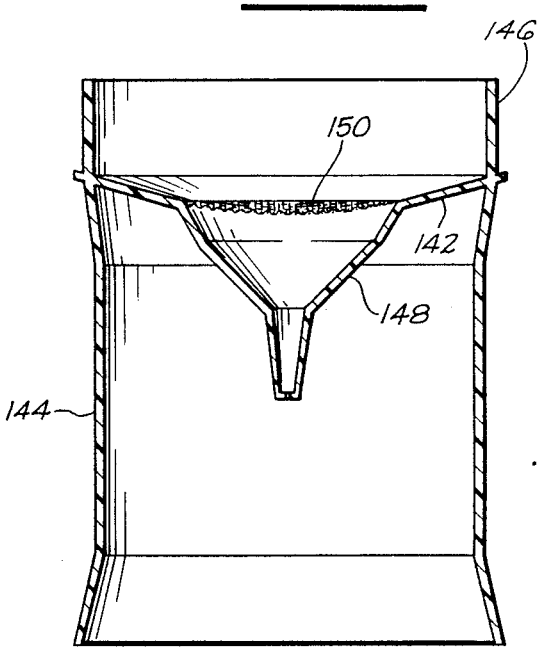
FIG. 10 is a cross section in side elevation of the flow rate controller of the apparatus of FIG. 1.

To this end, and as illustrated in FIGS. 1 and 10, the flow rate controller is comprised of a partition 142 having a depending skirt 144 that rests on the support member 84 to position the partition 142 above the receiver 110. (Notches 146 and 148, formed in the edge of the partition and the lower edge of the skirt and shown in FIG. 1, provide clearance for passing the wires 52 and 54 between the connectors 44, 48 and the reed switch 134.) A tubular flange 146 is formed on the partition 142 to extend upwardly adjacent the inner wall of the tubular portion 30 of the canister 22 and form a catchment for fluid entering a canister via the entry port formed by the connector 44. An upwardly opening funnel 148 is formed integrally in central portions of the partition to drain the catchment at a controlled rate into the receiver 110 so that, under high flow conditions, the flow rate controller will collect fluid in excess of quantities that can be measured by the volume indicator assembly 24 for subsequent drainage into the receiver 110 as the conclusion of the high rate of flow of fluid into the canister 22.

The flow rate controller can also provide a convenient mount for filters as shown in FIGS. 10 and 11, such FIG.s showing different forms and mounting of filters that can be used in the apparatus 20. As shown in FIG. 10, the filter can take the form of a screen 150 laid across the mouth of the funnel 148 or, as shown in FIG. 11, the filter can take the form of a porous membrane 152 secured by a plastic 0-ring 154 forced into the flange 146. As in the case of the filter 92, the filter 152 can be constructed of tightly woven silk cloth.

Referring now to FIGS. 12 and 13 and with continuing reference to FIG. 1, one preferred form of the discharge assembly, designated by the numeral 28, is comprised of a first pump assembly 154 that is, in turn, comprised of a first pump 156 and electric motor 158 as has been schematically indicated in FIG. 13. The pump 156 is fluidly communicated with the interior of the canister 22 via discharge port for the canister that is provided by a tubing connector 160 screwed into a threaded bore (not numerically designated in the drawings) formed through the floor plate 40 of the canister 22 and tubes 162, 164 and 166 that extend from the tubing connector 160 to the inlet of the pump 156 as indicated in FIG. 12 and schematically shown in FIG. 13. A valve 168 is connected between the tubes 162 and 164 and a valve 170 is similarly connected between the tubes 164 and 164. In the embodiment of the discharge system shown in FIGS. 12 and 13, the valve 168 is a conventional, manually operated shut-off valve that can be opened to fluidly communicate the tubes 162 and 164. The valve 170, on the other hand, is a manually operated three-way valve that has two open positions, one of which fluidly communicates the tubes 164 and 166 and the other of which fluidly communicates the tube 166 with a tube 172 whose purpose will become clear below, and a closed position in which the valve 170 blocks fluid flow into the tube 166. A tube 174 is connected to the outlet of the pump 156 for discharge of the effluent from the pump 156 to any convenient fluid receiver; for example, a drain.

As will be seen from the above description of the pump assembly 154 and the tubes and valves connecting such assembly to the canister 22, the canister 22 can be drained by opening the valves 168 and 170 to provide fluid communication between the tubing connector 160 and pump 156 and by then operating the motor 158. For the latter purpose, the motor 158 can be connected to any convenient power supply 176 via conductors 178, 180, and 182 and switch 184 as schematically indicated in FIG. 13. However, such operation can result in providing an avenue for infectious agents to a patient through the discharge assembly 28 and the canister 22. To prevent such an avenue from occurring, the apparatus 20 is further provided with a flushing assembly (not generally designated in the drawings) comprised of a second pumping assembly 178 that, like the pumping assembly 154 is comprised of a pump, referred to herein as a second pump 180, and electric motor 182. As schematically indicated in FIG. 13, the outlet of the second pump 180 is connected to the tube 172 that connects to the valve 170 and the inlet of the pump 180 is connected to an antiseptic reservoir 184, containing for example a fifteen percent sodium hypochlorite solution, via a tube 186. Thus, the pumping assembly 154 can be sterilized prior to discharging fluid from the canister 22, to prevent opening an avenue for infection by such discharge, by turning the valve 170 to communicate the tubes 166 and 172 and operating both motors 158 and 182. The latter operation is effected via conductors 188 and 190 and switch 192 that connect the motor 182 to the power supply 176. Conveniently, and as shown in FIG. 12, the reservoir 184 is a flexible plastic bag that can be mounted on the canister 22 by a hook 194 cemented to the side of the tubular portion 30 thereof and the pumping assemblies 154 and 178 can be mounted on a ledge 194 that is cemented on side of the portion 30 of the canister 22.

The discharge assembly 28 is particularly useful in circumstances in which only rudimentary medical facilities are available, the power supply in such circumstances preferably being an easily transportable battery pack. FIG. 14 illustrates the circuit diagram of a modified discharge assembly, designated 28A, which is especially useful in circumstances in which more extensive medical facilities are available.

The discharge assembly 28A differs from the discharge assembly 28 only in that the discharge assembly 28A is adapted for operation by the computer 62. Otherwise, the two assemblies are identical in construction.

Thus, it will not be necessary for purposes of disclosure to describe the discharge assembly 28A in detail; rather, parts of the assembly 20A that are identical to the discharge assembly 28 have been identically numbered in FIGS. 13 and 14 so that only the differences between the two discharge assemblies 28 and 28A need be describe with respect to FIG. 14.

The hydraulic circuit of the discharge assembly 28A differs from that of the discharge assembly 28 only in that the manually operated valves 168 and 170 of the assembly 28 are replaced with solenoid valves 168A and 170A, having the same fluid control characteristics as the valves 168 and 170 respectively, and the valves 168A and 170A are connected to the computer by conductors 198 through 206. Thus, fluid flow in the discharge assembly 28A can be controlled in the discharge assembly 28A by the computer 62 in the same manner that manual control is effected in the discharge assembly 28. Similarly, the only difference between the electrical circuits of the discharge assemblies 28 and 28A is that the motors 158 and 182 are connected via conductors 208 through 214 so that operation of the pump assemblies 154 and 178 is carried out by the computer 62 instead of by closing switches as in the operation of the pump assemblies of the discharge assembly 28.

OPERATION

To describe the operation of the apparatus 20, it will be useful to consider two applications to which the apparatus might be put: a uroflowmeter and a collection container for a mixture of blood and saline solution drawn from a wound during surgery. It will be understood that no limitations are to be implied by the selection of these two applications; rather such applications are merely exemplary of the wide range of uses to which the present invention might be put.

Prior to use of the apparatus 20 as a uroflowmeter, the electrical connector 56 is connected to the computer 62 via a suitable application board (not shown) mounted on the systems board of the computer. Depending upon the medical problem of the patient, the pH probe 64 and an additional probe 94 are emplaced on the canister as shown in FIG. 1 and suitable filters are placed in the canister as described above. If probes are used, they are connected to the computer via the application board; if they are not needed, they can be replaced with suitable plugs (not shown) to seal the canister 22. A program is then entered into the memory of the computer to continuously monitor closures of the reed switch 134 of the volume indicator assembly 24 and values of quantities measured by the probes 64 and 94. If the discharge assembly has the form shown in FIG. 14; that is the assembly 28A, the program will further specify conditions under which the discharge assembly 28A is to be operated; for example, the program can contain instructions to automatically empty the canister 22 after a measured volume of fluid has been introduced thereinto.

With the apparatus 20 readied in this manner, a length of tubing (not shown) is mounted on the tubing connector 48 forming the suction port and closed with a tubing clamp. A catheter is then extended from the tubing connector 44 that forms the entry port to the bladder of the patient. Thereafter, monitoring of the flow rate and other parameters selected by choice of probes 64 and 94 occurs continuously for display at any time. In particular, as urine is discharged by the bladder, the urine will enter the cup 72 on the underside of the cover plate 36 of the canister 22 via the catheter and will drip on the pH probe 64, if present, to continuously provide pH data to the computer 62. Thereafter, the urine will drip from the cup 72 to the funnel 148 of the flow rate controller and thence to the receiver 110 of the volume indicator assembly 24. Each time the selected increment of urine collects, in the receiver 110, the receiver will become imbalanced and will pivot from the position in which it is disposed to the other of the two positions shown in FIG. 7 to momentarily close the reed switch 134 so that the computer will count each increment of urine the patient has discharged.

When the receiver 110 pivots, the collected urine will be discharged into lower portions of the canister 22 where an additional parameter can be sensed by the probe 94, if such probe is present, and transmitted to the computer 62. Should it be desired, at any time to chemically analyze the urine, a hypodermic syringe can be used to withdraw a sample of the urine via a puncture formed through the disc 106 of the injection port 96.

Once a large quantity of urine collects, the discharge system is operated by the computer 62 to initially open the valve 170A to flow from the pump 180 through the pump 156 so that the discharge assembly 28A can be flushed with the antiseptic solution from the reservoir 184 as described above. Thereafter, the valves 168A and 170A are opened to provide fluid flow from the canister 22 to the pump 156 to drain the canister 22. Should the discharge assembly 28 be used in place of the discharge assembly 28A, these operations will, of course, be carried out by a human operator who selectively opens and closes the valves 168 and 170 and operates the switches 184 and 192 as described above. In this case, the human operator can be alerted to the need for draining the canister 22 by the computer 62 or by visually inspecting the canister 22 at selected intervals.

During surgery, the apparatus provides a convenient tool for continuously monitoring the loss of blood by the patient. In this case, following set-up of the apparatus 20 in the manner described above for use as a uroflowmeter, the suction port is connected to any vacuum source by a length of surgical tubing mounted on the tubing connector 48 and a length of tubing on the connector 44 provides for withdrawal of fluid from the wound.

At times that the surgeon wishes to check blood loss, he will introduce a measured quantity of saline solution into the wound and then draw the resulting mixture of blood and solution into the canister via the tube to the tubing connector 44. As will be clear to those skilled in the art, such fluid will be forcefully drawn into the cup 72 at a rapid rate and discharged via the perforations therein. The splash shield 80 will prevent the fluid rom being forced to the interior wall of the canister 22 so that the fluid will be discharged onto the partition 142 of the flow rate controller 26 to be collected by the catchment formed by the flange 146 and released at a controlled rate to the receiver 110 of the volume indicator assembly 24, such rate being selected by the construction of the funnel 148 to prevent overloading the operating rate of the volume indicator assembly 24. Thus, the receiver 110 will collect and discharge a succession of increments of fluid each having a known volume and the computer will continuously display the quantity of fluid withdrawn from the wound. Thus, the surgeon can determine the quantity of blood the patient has lost from the difference between the amount of fluid withdrawn from the wound and the amount of saline solution introduced thereinto. Further, he can similarly determine such loss independently of the computer display so that he has a back-up should the computer, for any reason, suffer a loss of operation. All he need do is determine the quantity of fluid withdrawn by observing the level of fluid through the transparent wall of the tubular portion 30 of the canister 22 against the indicia 32 inscribed thereon. Discharging of the canister 22 in this application of the apparatus 20 is effected as described above.

In the blood loss monitoring application of the apparatus 20, the injection port 96 has a use that is in addition to the sampling of the contents of the canister 22. Should any tendency of the fluid to form clots be detected, the injection port forms a convenient entry point for the introduction of an anticoagulant into the mixture of blood and saline solution in the canister 22.

It will be clear that the present invention is well adapted to carry out the objects and attain the ends and advantages mentioned as well as those inherent therein. While presently preferred embodiments have been described for purposes of this disclosure, numerous changes may be made which will readily suggest themselves to those skilled in the art and which are encompassed in the spirit of the invention disclosed and as defined in the appended claims.

What is claimed is:

1. A fluid monitoring apparatus comprising:
    a canister having a tubular body portion with an upper end and a lower end;
    a cover plate extending across the upper end of the tubular body portion of the canister, the cover plate having an entry port for introduction of liquid into the tubular body portion and a suction port so that air pressure within the tubular body portion can be lowered for drawing fluid into the entry port;
    a floor plate extending across the lower portion of the tubular body portion of the canister;
    volume indicator means disposed within the tubular body portion of the canister below the entry port for receiving the fluid introduced into the tubular body portion and providing an electrically sensible indication for each of a series of selected volume increments of fluid introduced into the tubular body portion of the canister;
    flow rate control means disposed between the entry port and the volume indicator means for limiting the flow rate of flow of fluid into the volume indicator means; and
    a fluid separator mounted on the cover plate so as to be disposed within the tubular body portion of the canister, the fluid separator comprising:
        a perforated cylindrical cup secured to the cover plate so as to extend about the entry and suction ports; and
        a partition plate extending diametrically across the perforated cylindrical cup between the entry port and the suction port so as to divide the perforated cylindrical cup into non-communicating entry and suction chambers.

2. The apparatus of claim 1 wherein the flow rate control means comprises:
    a partition extending laterally across an upper portion of the tubular body portion of the canister, the partition having an upwardly extending tubular flange formed thereon for collecting fluid introduced into the tubular body portion of the canister, the partition having an upwardly opening funnel portion formed integrally therein above the volume indicator means for discharging fluid at a controlled rate into the volume indicator means.

3. The apparatus of claim 2 further comprising:
    a filter extending across the top of the funnel portion of the partition of the flow rate control means.

4. The apparatus of claim 3 wherein the filter is characterized as being a porous membrane.

5. The apparatus of claim 1 wherein the tubular body portion of the canister is formed of a transparent material and 6. The apparatus of claim 1 further comprising:
    a tubular splash shield attached to the cover plate so as to be disposed within the tubular body portion of the canister and extend in a concentric relation about the perforated cup.

7. The apparatus of claim 1 further comprising:
    a cylindrical pH probe mounted in the cover plate to extend into portions of the tubular body portion of the canister so as to be disposed below the entry port.

8. The apparatus of claim 1 wherein the tubular body portion of the canister is further provided with a sensor probe opening formed through a lower portion of the tubular body portion, and wherein the apparatus further comprises:
    means mounted in the sensor probe opening for mounting a cylindrical sensor probe with the sensor probe 9. The apparatus of claim 1 wherein a a lower portion of the tubular body portion of the canister is provided with a discharge port, and wherein the apparatus further comprises:
    pumping means fluidly communicating with the interior of the tubular body portion via the discharge port for pumping fluid from the tubular body portion of the canister.

10. A fluid monitoring apparatus comprising:
    a canister having a tubular body portion, an upper end and a lower end, the upper end having an entry port formed therein for introduction of fluid into the canister, the tubular body portion further provided with an injection opening formed through a lower portion thereof;
    volume indicator means disposed within the canister below the entry port for receiving fluid introduced into the canister and providing an electrically sensible indication for each of a series of selected volume increments of fluid introduced into the canister;
    flow rate control means disposed between the entry port and the volume indicator means for limiting the rate of flow of fluid into the volume indicator means;
    a disc formed of an elastomeric material extending across the injection opening; and
    means for mounting the disc on the tubular body portion of the canister.

* * * * *

UNITED STATES PATENT AND TRADEMARK OFFICE
CERTIFICATE OF CORRECTION

PATENT NO. : 4,955,391

DATED : September 11, 1990

INVENTOR(S) : Robert L. Parker and Charles G. Reed

It is certified that error appears in the above-identified patent and that said Letters Patent is hereby corrected as shown below:

Column 1, line 7, delete "No." and substitute therefor --Application--;

Column 1, line 57, before "this purpose" insert --for--;

Column 4, line 37, after "with" delete "a" and substitute therefor --an--;

Column 4, line 64, delete "the to" and substitute therefor --to the--;

Column 5, line 23, before "angled" delete "an" and substitute therefor --and--;

Column 5, line 28, delete "assemble 24" and substitute therefor --assembly 24--;

Column 5, line 50, delete "portion, 30" and substitute therefor --portion 30--;

Column 8, line 6, delete "164." and substitute therefor --166.--;

Column 12, line 17 (claim 5), after "and" insert --wherein volume indicia are inscribed on the tubular body portion below the volume indicator means.--;

Column 12, line 35, after "probe" insert --opening such that the sensor probe extends into the interior of the tubular body portion of the canister.--;

UNITED STATES PATENT AND TRADEMARK OFFICE
CERTIFICATE OF CORRECTION

PATENT NO. : 4,955,391

DATED : September 11, 1990

INVENTOR(S) : Robert L. Parker and Charles G. Reed

It is certified that error appears in the above-identified patent and that said Letters Patent is hereby corrected as shown below:

Column 12, line 36, delete "a a" and substitute therefor --a--; and

Column 12, line 40, delete "communicating" and substitute therefor --communicated--.

Signed and Sealed this

Seventh Day of July, 1992

Attest:

DOUGLAS B. COMER

*Attesting Officer*       *Acting Commissioner of Patents and Trademarks*